United States Patent

Yankielun et al.

[11] Patent Number: 5,804,721
[45] Date of Patent: Sep. 8, 1998

[54] CAPACITOR FOR WATER LEAK DETECTION IN ROOFING STRUCTURES

[76] Inventors: Norbert E. Yankielun, 54 Nottingham Cir., Lebanon, N.H. 03766; Stephen N. Flanders, 317 Hopson Rd., Norwich, Vt. 05055-9442

[21] Appl. No.: 800,498

[22] Filed: Feb. 14, 1997

[51] Int. Cl.[6] .................................................. G01N 37/00
[52] U.S. Cl. ........................................................ 73/335.04
[58] Field of Search .......................... 73/29.01, 335.04, 73/73, 40

[56] References Cited

U.S. PATENT DOCUMENTS

| | | | |
|---|---|---|---|
| 2,047,638 | 7/1936 | Kott | ............................ 73/73 |
| 2,461,310 | 2/1949 | Cilley . | |
| 2,649,579 | 8/1953 | Alexander . | |
| 2,944,199 | 7/1960 | Hudson . | |
| 3,353,025 | 11/1967 | Sturm . | |
| 4,051,721 | 10/1977 | Williams . | |
| 4,096,758 | 6/1978 | Moore . | |
| 4,125,822 | 11/1978 | Perren et al. | ............................ 73/40 X |
| 4,662,220 | 5/1987 | Laue . | |
| 4,926,165 | 5/1990 | Lahlouh et al. | ........................ 73/40 X |
| 5,348,761 | 9/1994 | Mitter et al. . | |
| 5,563,341 | 10/1996 | Fenner et al. . | |

Primary Examiner—Hezron E. Williams
Assistant Examiner—Daniel S. Larkin
Attorney, Agent, or Firm—Luther A. Marsh

[57] ABSTRACT

A pair of metal plates having a space therebetween are surrounded by a flexible enclosure which is waterproof and which is filled with a dry gas. A pair of electrical conductors connected to the plates extend through and are water-tight sealed to the enclosure. A water-deformable element which expands in the presence of moisture is disposed around the enclosure, and a rigid housing having holes therethrough is disposed around the water-deformable element so that moisture passing through the holes into the water-deformable element causes it to expand to move the enclosure and at least one plate so as to reduce the space between the plates to change the capacitance of the capacitor.

11 Claims, 1 Drawing Sheet

FIG.1.
FIG.2.
FIG.3.
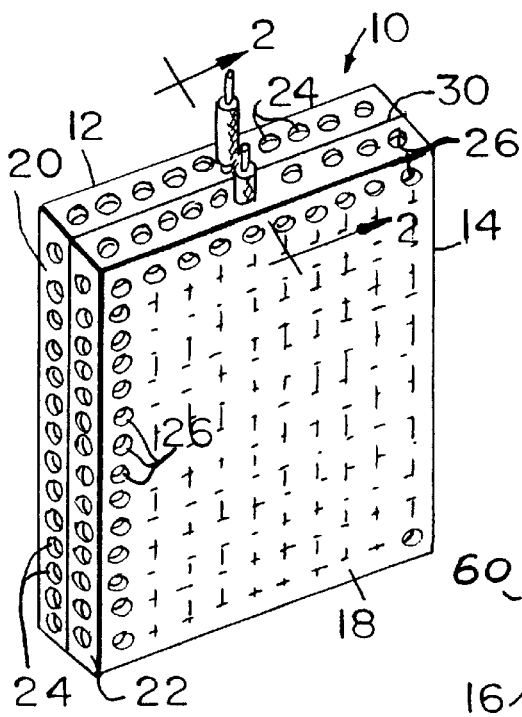
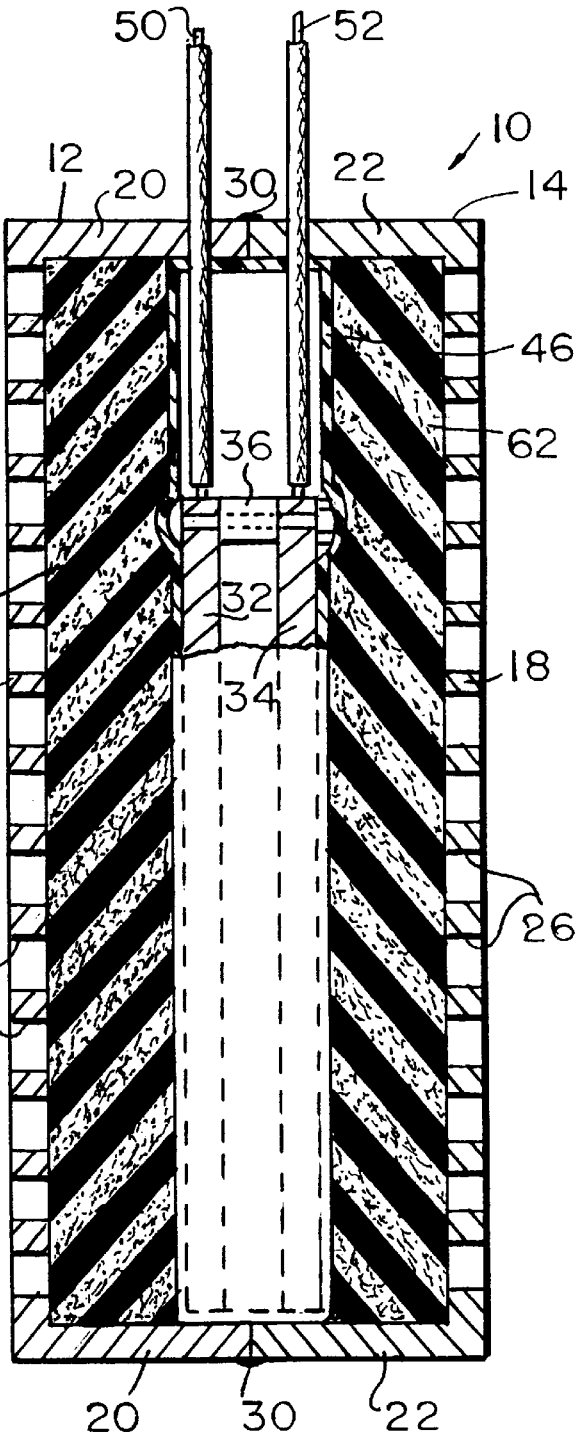
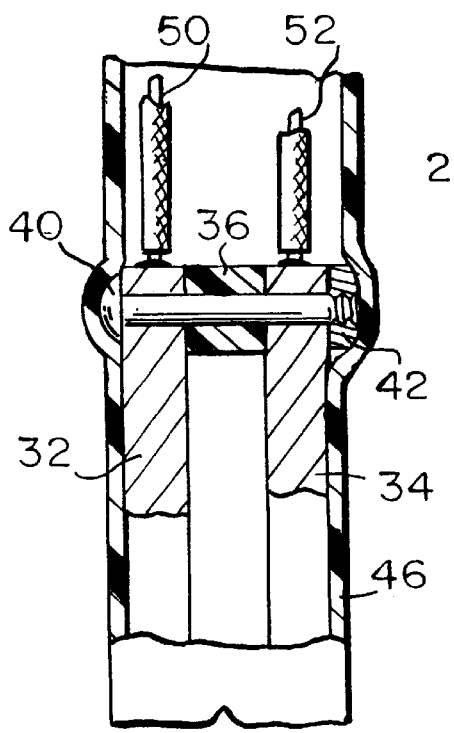

CAPACITOR FOR WATER LEAK DETECTION IN ROOFING STRUCTURES

BACKGROUND OF THE INVENTION

The present invention relates to a moisture sensitive capacitor, and more particularly to a capacitor which is especially adapted to be used for water leak detection in roofing structures. The capacitor is adapted to be connected in an inductor-capacitor resonant circuit in a conventional detector apparatus wherein changes in capacitance result in changes in the resonant frequency of the circuit which is utilized in a well-known manner to provide an indication of the presence of water moisture.

It is, of course, understood that the capacitor of the invention may also be used in other fluid-sensing applications other than in roofing structures. The invention may be used for sensing the presence or absence of a wide variety of lossy and/or conductive fluids as well as low-loss and/or nonconductive fluids.

Moisture sensitive capacitors operating in dry to low-moisture or conditions can tolerate moisture in contact with the plates of the capacitor. However, under high moisture and saturated conditions, prior art capacitors do not function in a satisfactory manner. In the case of a hydrophilic dielectric material disposed between the plates of a capacitor, the dielectric losses imposed on the capacitor by plate-to-plate contact with water increase the dissipation or leakage of the capacitor, thereby decreasing the inductor-capacitor circuit "Q" to a point where resonance can no longer be determined. This is not acceptable where a frequency shift in resonance of the detection circuit due to increased intra-plate moisture is desired. Likewise, in the case of air dielectric capacitors, under saturation conditions, unsatisfactory results are obtained where a frequency shift in resonance of the detection circuit is desired.

It is therefore a primary objective of the invention to provide a moisture sensitive capacitor which provides good results where a frequency shift in resonance of the detection circuit is desired even under high moisture and saturated conditions.

SUMMARY OF THE INVENTION

The capacitor of the invention effectively operates in the frequency shift mode from moderate moisture levels to complete! inundation. This is accomplished by providing a novel construction wherein a pair of electrically conductive members or plates are surrounded by a flexible waterproof enclosure which ensures that moisture never comes into contact with the plates of the capacitor. A pair of electrical conductors are connected to the plates and pass outwardly through the enclosure and are water-tight sealed to the enclosure.

A water-deformable element is disposed outwardly of the enclosure and is formed of a material such as cellular sponge which expands in the presence of moisture. A rigid housing is disposed outwardly of the water-deformable element and has a plurality of holes formed therein through which water can flow into and out of the water-deformable element. As water flows into the element, the rigid housing contains the swelling and the increased volume of the element applies inward pressure on the flexible enclosure.

The plates within the enclosure are normally spaced from one another, but are adapted to move toward and away from one another so that when inward pressure is applied to the flexible enclosure, one or both plates are caused to move so as to reduce the space between the plates. As this space is reduced, the capacitance of the capacitor is increased, causing a lower resonant frequency in an associated detecting circuit including an inductor coupled to the capacitor. In this manner, the capacitor successfully operates in the frequency shift mode even under saturated conditions since the plates of the capacitor do not come in contact with water. The space within the enclosure is filled with a dry gas such as air to provide the desired dielectric for the capacitor.

The invention provides a low dissipation capacitor which will, maintain high "Q" in an inductor-capacitor resonant circuit and permits a frequency shift resonant indication of moisture presence. It also enables sensing the presence or absence of fluids that would otherwise present lossy or conductive conditions to a capacitive sensor.

BRIEF DESCRIPTION OF THE DRAWINGS

FIG. 1 is a top perspective view of the invention capacitor;

FIG. 2 is an enlarged sectional view on line 2—2 of FIG. 1; and

FIG. 3 is an enlarged view of a portion of the structure shown in FIG. 2.

DESCRIPTION OF THE PREFERRED EMBODIMENT

Referring now to the drawings wherein like reference characters designate corresponding parts throughout the several views, a housing 10 formed of relatively rigid plastic comprises two similar halves 12 and 14 which have side walls 16 and 18 respectively of generally square configuration as shown in FIG. 1. End walls 20 and 22 extend from the outer peripheries of the side walls 16 and 18 respectively on all four sides of the side walls, the endwalls being disposed at right angles to the side walls. The side and end walls of the two halves 12 and 14 of the housing are provided with a plurality of holes 24 and 26 respectively formed through the side and end walls thereof to permit moisture to flow into and out of the interior of the housing. The holes are distributed over the outer surface of the housing so that the holes comprise a substantial portion of the total area of such outer surface as is apparent from the drawings.

The two halves of the housing are suitably sealed to one another as by heat sealing opposing edges of the end walls of the two halves as indicated by reference numeral 30. It is apparent that the housing may be of many different configurations.

Disposed within the housing are a pair of capacitor plates 32 and 34 in the form of electrically conductive members typically formed of metallic material such as copper, brass or aluminum and the like. The plates may be of flat rectangular configuration and are disposed in spaced parallel relationship to one another. The plates are sufficiently thin that they may be readily deformed since it is necessary to move one or both of the plates during operation to reduce the space between the plates and thereby vary the capacitance of the capacitor. The plates may also be of other configurations such as cylindrical wherein one of the plates is disposed in coaxial spaced relationship to the other plate, if so desired.

Referring to FIG. 3, a spacer 36 is disposed between the upper ends of plates 32 and 34 for maintaining the plates is spaced relationship. The spacer is formed of dielectric material such as nylon. A nylon screw 40 extends through suitable holes provided in plates 32 and 34 and spacer 36, a nylon nut 42 being threaded on the outer threaded end of the screw for retaining the spacer in operative position with the plates spaced from one another. Other suitable spacer means may be provided for normally retaining the plates in spaced relationship, while allowing one or both of the plates to be deformed to reduce the space between the plates.

Referring to FIG. 2, an enclosure is provided for the plates in the form of a flexible waterproof membrane 46 which may be formed of Mylar or a latex material. Enclosure 46 completely surrounds the plates and is completely sealed with respect thereto so that no moisture may come into contact with the plates. While the enclosure is shown as being flexible throughout, it is only necessary that the enclosure have a flexible portion adjacent at least one of the plates so as to be capable of deforming one plate under certain conditions. Of course, as shown, the enclosure is flexible adjacent both of the plates so that the plates may both be deformed toward one another.

The enclosure is filled with a dry gas such as air or nitrogen to provide a suitable dielectric material between the plates, and further to maintain the enclosure in the shape shown in surrounding relationship to the plates.

A pair of insulated electrical conductors 50 and 52 are connected to plates 32 and 34 respectively, these conductors passing through the enclosure membrane 46 and being water-tight sealed with respect to the membrane as by heat sealing.

A first body of water-deformable material 60 is disposed within housing portion 12 and is adjacent one side of enclosure membrane 46. A second body of water-deformable material 62 is disposed within housing portion 14 and adjacent the opposite side of enclosure membrane 46. Bodies 60 and 62 preferably substantially fill the space between the side walls of housing portions 12 and 14 and the the enclosure membrane. The water-deformable material is formed of cellular sponge material or blotter paper, for example. These substances readily absorb moisture and have a minimum volume when dry and expand when wet.

In the presence of moisture, the water-deformable material expands, but the rigid housing prevents the material from expanding outwardly. Accordingly, as the material expands, it swells inwardly thereby applying pressure to the adjacent flexible enclosure portions to thereby move the flexible enclosure portions and the adjacent plates inwardly to reduce the space between the plates and change the capacitance of the capacitor. As the water-deformable material dries, it will shrink, allowing the plates to move toward their normal spaced apart positions. As noted previously, both plates move in the illustrated embodiment, but it is only necessary to move one of the plates.

The invention has been described with reference to a preferred embodiment. Obviously, various modifications, alterations and other embodiments will occur to others upon reading and understanding this specification. It is our intention to include all such modifications, alterations and alternate embodiments insofar as they come within the scope of the appended claims or the equivalent thereof.

What is claimed is:

1. A moisture sensitive capacitor comprising, a pair of electrically conductive members having a space therebetween, a flexible waterproof means disposed adjacent said members and preventing moisture from contacting said members, water-deformable means disposed adjacent said waterproof means, said water-deformable means expanding in the presence of moisture to move said waterproof means and at least one of said members to reduce said space between said members, and a relatively rigid means disposed adjacent said water-deformable means for limiting movement of said water-deformable means and permitting water to flow into and out of said water-deformable means.

2. A moisture sensitive capacitor comprising, a pair of electrically conductive members having a space therebetween, an enclosure surrounding said members, said enclosure being substantially waterproof and including a flexible portion, water-deformable means disposed outwardly of said flexible portion, said water-deformable means expanding in the presence of moisture to move said flexible portion and at least one of said members to reduce said space between said members, and a relatively rigid housing disposed outwardly of said water-deformable means and including opening means permitting water to flow into and out of said water-deformable means.

3. A capacitor as defined in claim 2 including a dry gas disposed within said enclosure.

4. A capacitor as defined in claim 2 including a pair of electrical conductors connected to said members, said conductors passing through said enclosure and being water-tight sealed with respect thereto.

5. A capacitor as defined in claim 2 including spacer means for maintaining said members in spaced relationship, said spacer means permitting movement of one of said members relative to the other.

6. A capacitor as defined in claim 5 wherein said spacer means comprises a spacer formed of dielectric material, said spacer being disposed between and engaging said members, and retainer means for retaining said spacer in operative position.

7. A capacitor as defined in claim 2 wherein said members comprise flat deformable metallic plates disposed substantially parallel with one another.

8. A capacitor as defined in claim 2 wherein said water-deformable means is formed of cellular sponge material.

9. A capacitor as defined in claim 2 wherein said water-deformable means is formed of blotter paper.

10. A capacitor as defined in claim 2 wherein said enclosure is formed of flexible plastic material.

11. A capacitor as defined in claim 2 wherein said housing has an outer surface, said opening means comprising a plurality of holes distributed over the housing so that the holes comprise a substantial portion of the total area of said outer surface to permit moisture to freely flow into and out of said water-deformable means.

\* \* \* \* \*